United States Patent [19]

Swindle et al.

[11] Patent Number: 5,893,865

[45] Date of Patent: Apr. 13, 1999

[54] APPARATUS AND METHOD FOR IMPROVED AORTIC INCISION

[75] Inventors: Carl A. Swindle, Irvine, Calif.; John C. Alexander, Jr., Kenilworth, Ill.

[73] Assignee: Baxter Research Medical, Inc., Midvale, Utah

[21] Appl. No.: 08/935,816

[22] Filed: Sep. 23, 1997

[51] Int. Cl.$^6$ ................................................ A61B 17/00
[52] U.S. Cl. ........................ 606/185; 30/366; 606/153
[58] Field of Search ................................ 606/1, 167, 170, 606/184, 185, 153; 30/366; 604/164

[56] References Cited

U.S. PATENT DOCUMENTS 5,624,459   4/1997   Kortenbach et al. ................... 606/185

*Primary Examiner*—Glenn K. Dawson
*Assistant Examiner*—William Lewis
*Attorney, Agent, or Firm*—Workman, Nydegger & Seeley

[57] ABSTRACT

An aortic knife which provides multi-sided incisions within an aorta for effectuating improved aortotomies. The aortic knife includes a handle and multiple blades radiating from the handle. The handle is sized and configured to maximize grip and surgical manipulation thereof. The multiple blades radiate outwardly and proximally from a distal sharpened point. A substantially cruciate, or cross-shaped, incision results from four sharpened blades extending from the distal sharpened point. Alternatively, the multi-bladed configuration of the aortic knife may comprise three, five, or six or more blades. The blades form equal angles in radiation outwardly and proximally from the distal sharpened point. The method of the invention requires obtaining an appropriately sized aortic knife which is stabbed into a portion of an aorta. An anvil of an aortic punch is then inserted into the incision in the aorta without the stretching necessitated by the conventional single linear incision. The punch is then centered and fired; the resulting aortotomy lacks the lateral nicks associated with the prior art. Alternatively, the knife may be used for cannulation of a vessel.

7 Claims, 5 Drawing Sheets

APPARATUS AND METHOD FOR IMPROVED AORTIC INCISION

BACKGROUND OF THE INVENTION

1. The Field of the Invention

The present invention is directed generally to methods and apparatus for effectuating surgical incisions. More specifically, the present invention is related to methods and apparatus for effectuating precise and uniform aortic incisions.

2. The Relevant Technology

Coronary artery bypass surgery is commonly required when coronary arteries narrowed by cholesterol-rich fatty deposits or plaques are unable to supply the heart muscle with a sufficient amount of blood, and as a result, the heart becomes starved for oxygen. Left untreated, coronary artery disease ultimately leads to acute myocardial infarction, commonly referred to as a heart attack. In coronary artery bypass surgery, a surgeon grafts a section of a healthy vessel, such as a portion of a saphenous vein, to bypass a stenotic or partially blocked portion of a coronary artery in order to ameliorate the oxygen access to the heart muscle.

Various techniques have been used to create the opening in the aorta, known as an aortotomy, to which the graft is sutured. Most aortotomies used for bypass grafts are created using a surgical scalpel in concert with an aortic punch. The surgical scalpel is used to make a linear incision in the aorta. Then, a portion of the aortic punch known as the "anvil" is passed through the incision. The punch is then engaged creating an aortotomy.

Conventionally, in order for the anvil of the punch to pass through the linear incision, either the incision needs to be longer than the diameter of the anvil or the hole created by the incision needs to be stretched. When the incision is made longer than the punch diameter, lateral nicks in the circumference of the aortotomy are created. These lateral nicks necessitate either repunching the aorta to enlarge the aortotomy or special suturing to avert bleeding at the lateral incision sites. Alternatively, when the initial hole created by the incision is stretched, often by utilizing a dilator prior to inserting the punch, an irregular and unpredictable tearing of the aorta often occurs.

The brittle and fragile nature of the aorta in the average coronary artery bypass graft patient necessitates great care in dealing with the aortic wall. The problems associated with conventional aortotomies can cause major problems with bleeding, compromise of the anastomosis, or aortic dissection.

SUMMARY AND OBJECTS OF THE INVENTION

It is therefore a primary object of the present invention to provide improved methods and apparatus for providing aortotomies for coronary artery bypass grafts.

It is another object of the present invention to provide improved methods and apparatus for providing precise and uniform aortotomies.

It is still another object of the present invention to provide improved methods and apparatus for providing aortotomies which do not require stretching or repunching.

These and other objects and features of the present invention will become more fully apparent from the following description and appended claims, or may be learned by the practice of the invention as set forth hereinafter.

The present invention is directed to an aortic knife which provides the unique feature of multi-sided incisions within an aorta for effectuating improved aortotomies. The aortic knife preferably includes multiple surgical blades connected to a handle portion. The handle is sized and configured to maximize grip and surgical manipulation thereof. The multiple blades extend to a distal sharpened point and radiate outwardly and proximally from the sharpened point. A preferred aortic knife provides a substantially cruciate, or cross-shaped, incision with four sharpened blades extending from the distal sharpened point.

Alternatively, the multi-bladed configuration of the surgical knife may comprise three, five, or six or more blades. It is preferred that the blades form equal angles in radiation outwardly and proximally from the distal sharpened point.

In a preferred method of the present invention, an appropriately sized aortic knife is obtained and stabbed into a portion of an aorta. An anvil of an aortic punch is then inserted into the incision in the aorta, a step that may be performed without the stretching necessitated by the conventional single linear incision. The punch is then centered and fired. The resulting aortotomy lacks the lateral nicks and aortic dissection associated with the prior art.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

In coronary artery bypass surgery, a surgeon grafts a section of a healthy vessel, such as a portion of the saphenous vein or other suitable material, to bypass a partially blocked portion of a coronary artery in order to improve the oxygen delivery to the heart muscle. Various techniques have been used to create the opening in the aorta, known as an aortotomy, to which the graft is sutured. Most aortotomies used for bypass grafts are created using a surgical scalpel in concert with an aortic punch. However, this conventional technique is imprecise at best, and the resulting graft is often compromised.

Figure 1:
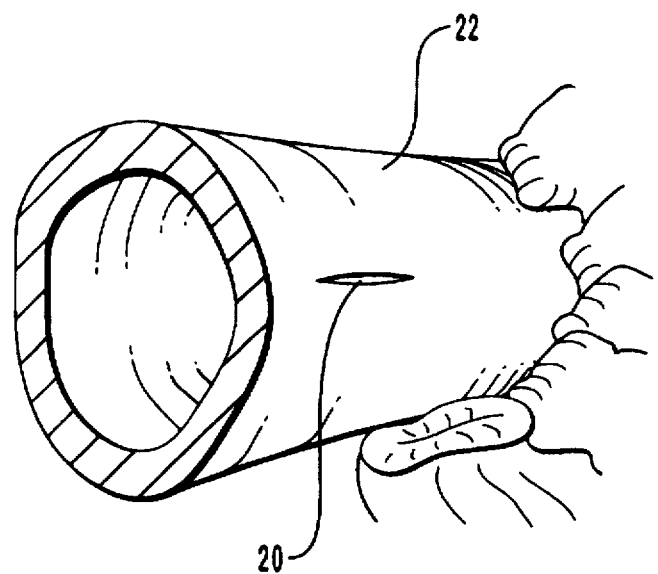
FIG. 1 is an illustration of an incision in an aorta provided by a conventional scalpel.
Figure 2:
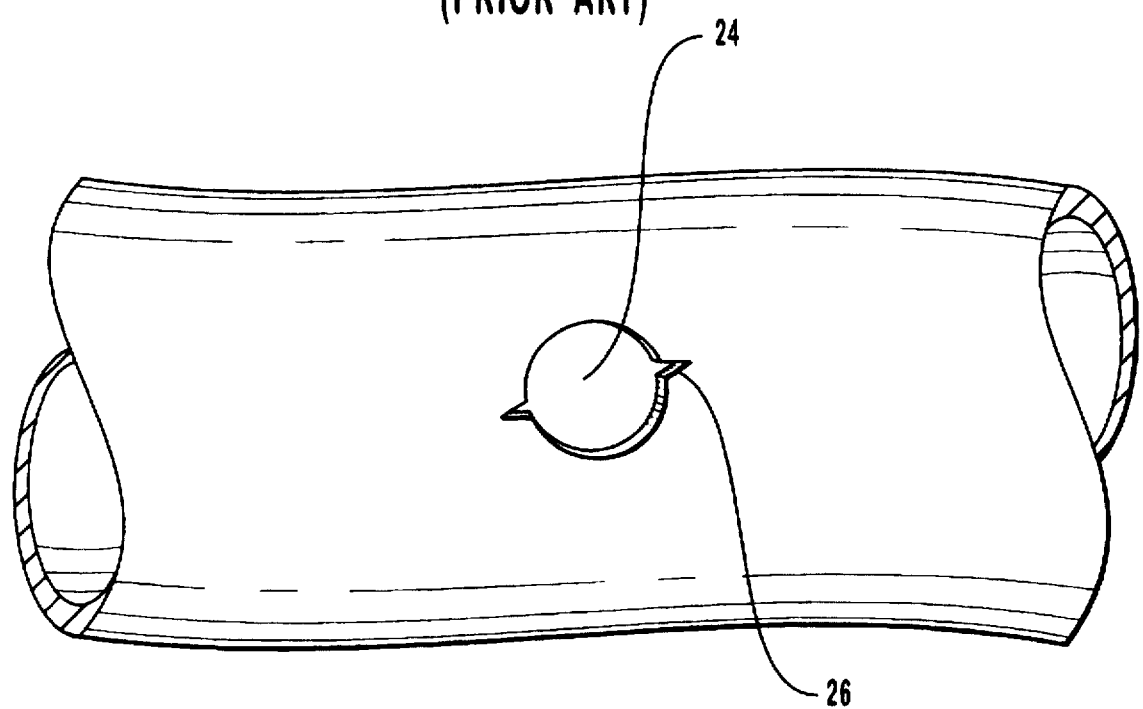
FIG. 2 is an illustration of an aortotomy resulting from an aortic punch used in concert with the incision in FIG. 1.

FIG. 1, for example, illustrates a conventional linear incision 20 along an aorta 22 utilizing a conventional scalpel. In performing such an incision, the surgeon makes an educated guess as to the length of the incision. FIG. 2 illustrates the resulting aortotomy 24 wherein lateral nicks 26 are clearly visible. These nicks necessitate special suturing to prevent blood leakage, and add points of weakness at the site of the vessel graft.

Alternatively, a surgeon may make an incision that is smaller than the diameter of the punch such that lateral nicks might be avoided. However, such an incision necessitates stretching of the tissue for insertion of the aortic punch anvil. In turn, the stretching of the tissue can decrease the patency of the resulting graft or can cause aortic dissection wherein the layers of the aortic wall separate from one another.

Figure 3:
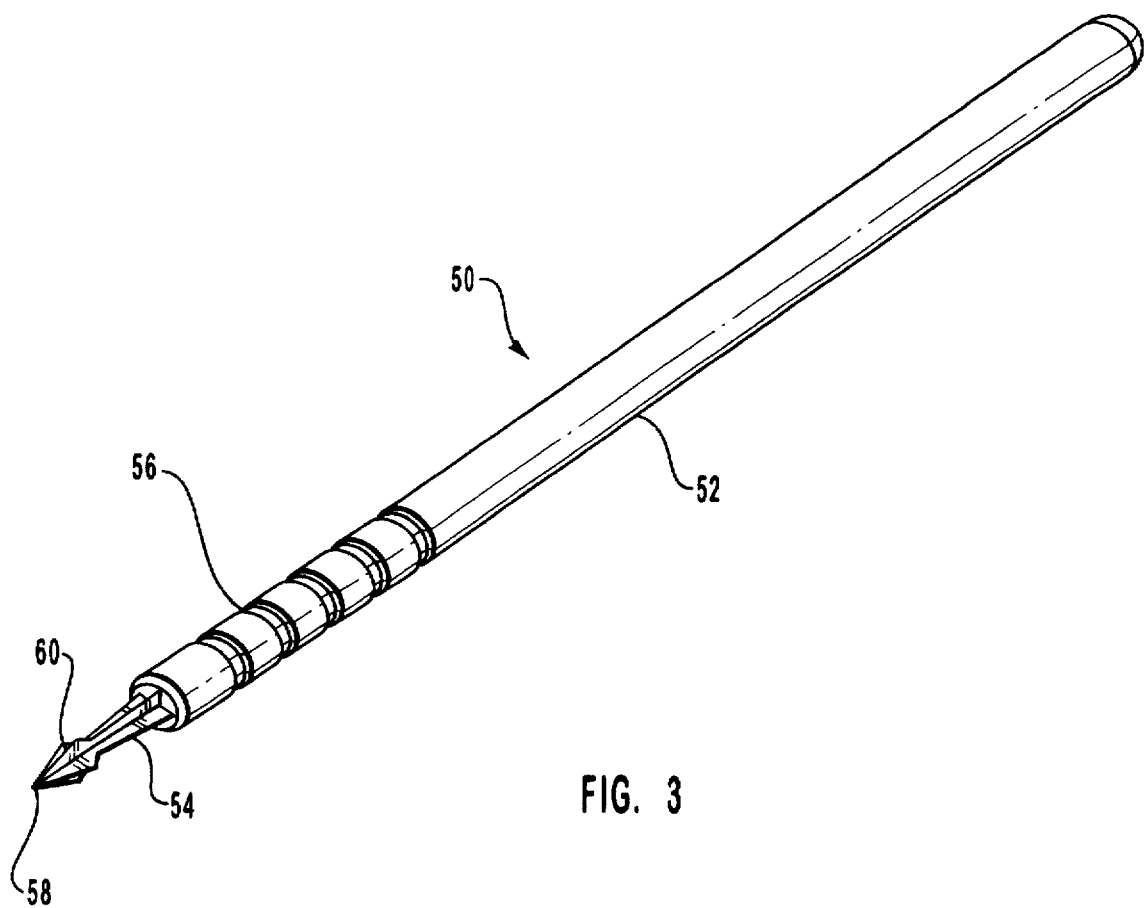
FIG. 3 is a partial perspective view of one embodiment of an aortic knife in accordance with the present invention.

In contrast, the present invention is directed to a precisely-sized, multi-bladed knife for effectuating an improved aortic incision and for significantly improving a surgeon's ability to create a proximal anastomotic site. FIG. 3, for example, illustrates one preferred embodiment of the present invention, represented generally by numeral 50. The aortic knife of the present invention preferably includes a surgical knife with multiple blades 54 attached to a handle 52.

The handle 52 preferably comprises a rigid material such as steel, plastic, or wood. As should be appreciated by reference to FIG. 3, the handle includes a grip portion 56 to improve a surgeon's grasp and prevent slipping of the knife. The handle is preferably sized to maximize surgical manipulation thereof.

Further, the aortic knife preferably comprises a multi-bladed portion, as illustrated generally by numeral 54 in FIG. 3. The multiple blades are preferably formed from surgical steel.

Figure 4:
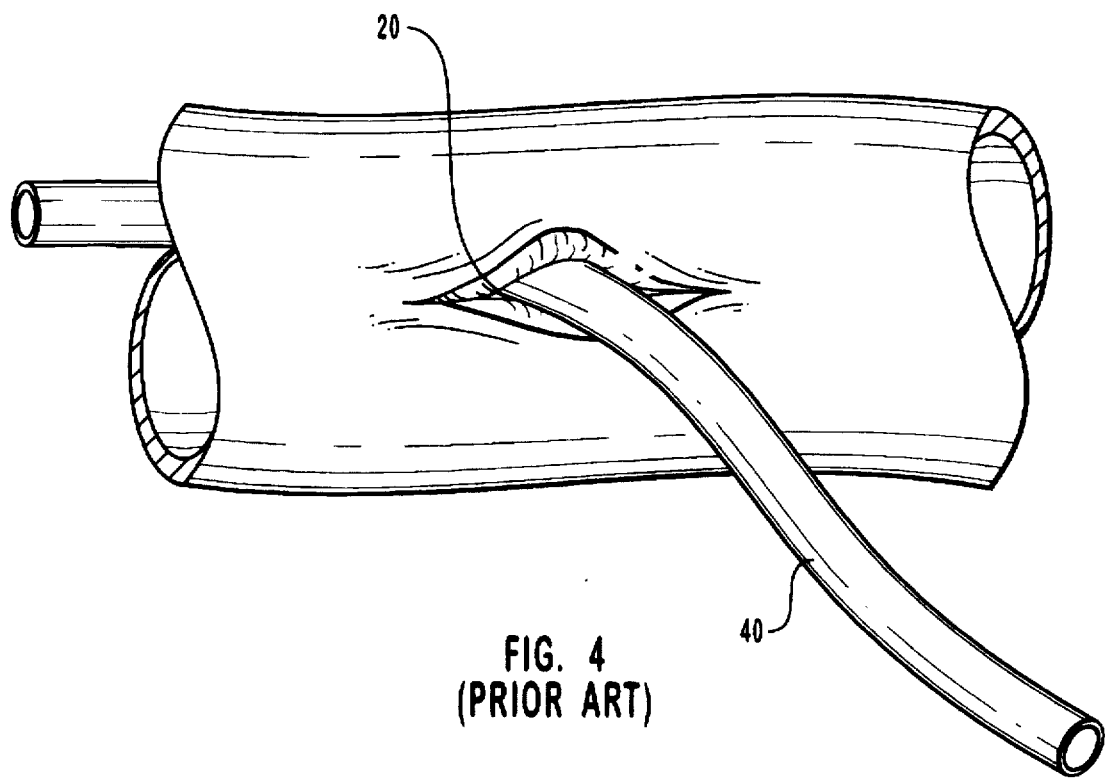
FIG. 4 is an illustration of cannulation through an incision in a vessel provided by a conventional scalpel.
Figure 5:
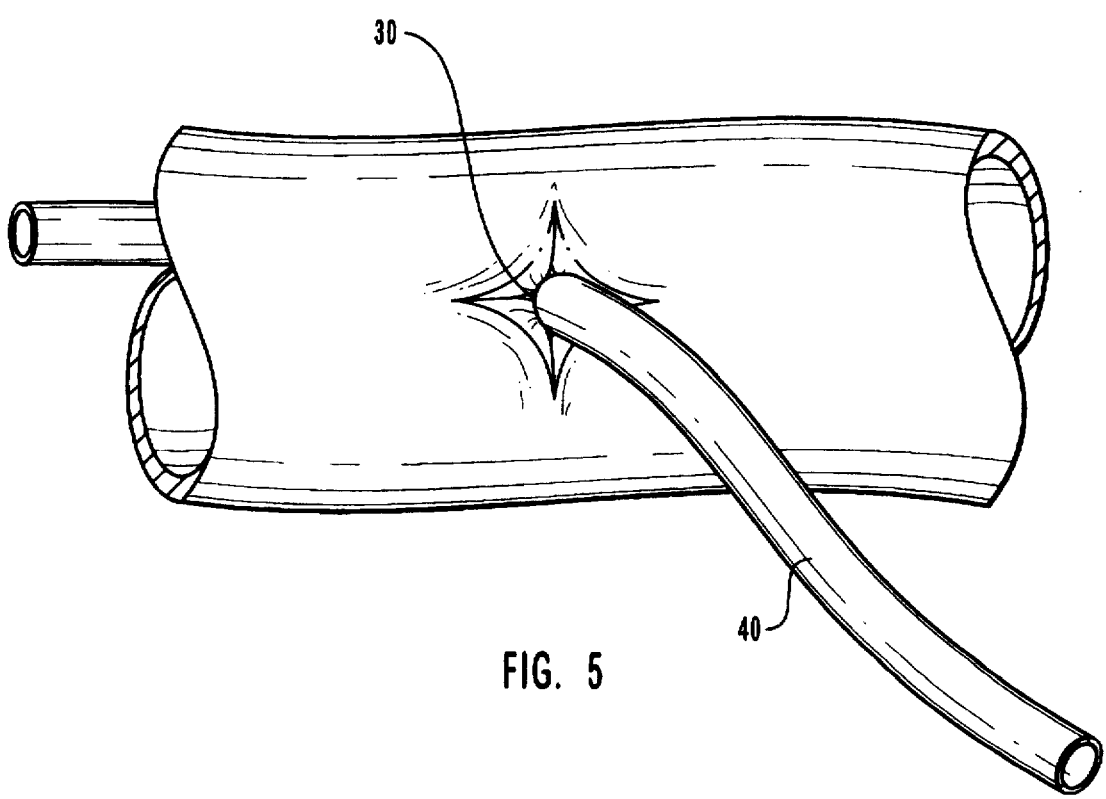
FIG. 5 is an illustration of cannulation through an incision in a vessel provided by an aortic knife in accordance with the present invention.

The multi-bladed configuration of the aortic knife provides multiple cutting surfaces, which results in an incision which displaces the tissue in multiple directions, and facilitates insertion of medical devices such as cannulae or aortic punches. When a surgical instrument is introduced into the multi-sided incision, the tissue displaces circumferentially around the instrument, whereas the conventional incision results in linear tissue displacement which requires the tissue to stretch around the instrument. FIG. 4, for example, illustrates the linear tissue displacement which occurs upon the insertion of a cannula 40 through a conventional incision 20. In contrast, FIG. 5 illustrates the inward and circumferential tissue displacement around the cannula 40 when the cannula is introduced into a multi-sided incision 30 in accordance with the present invention.

In a preferred embodiment of the present invention, the aortic knife comprises four blades, each blade being separated from each other blade by 90 degrees. The resulting shape of the incision is substantially cruciate or cross-shaped, and thus substantially resembles a "+" configuration. As illustrated in FIG. 3, the multiple blades of the aortic knife 54 preferably extend distally to a sharpened point 58, which facilitates perpendicular insertion of the aortic knife into the aorta or other vessel. Each of the plurality of sharpened sides 60 radiates outwardly and proximally from the sharpened distal point 58.

Once the sharpened distal point 58 is perpendicularly stabbed into a vessel, the sharpened sides slide into the vessel and provide the unique and improved incision of the present invention. The resulting incisions are situated circumferentially around the central stabbed portion, which effectuates inward displacement of the tissue in four directions upon insertion of a surgical instrument. The preferred four-sided, or cruciate, incision of the present invention facilitates insertion of a punch anvil and thus reduces trauma to the aortic wall.

Figure 6:
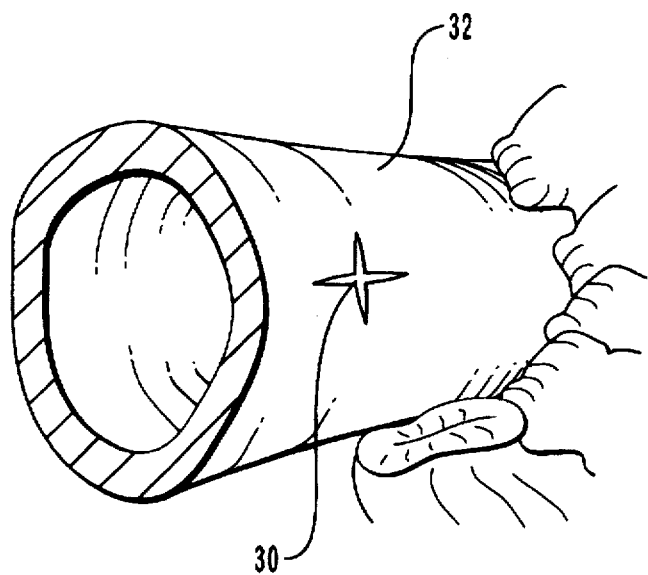
FIG. 6 is an illustration of an incision in an aorta provided by an aortic knife in accordance with the present invention.
Figure 7:
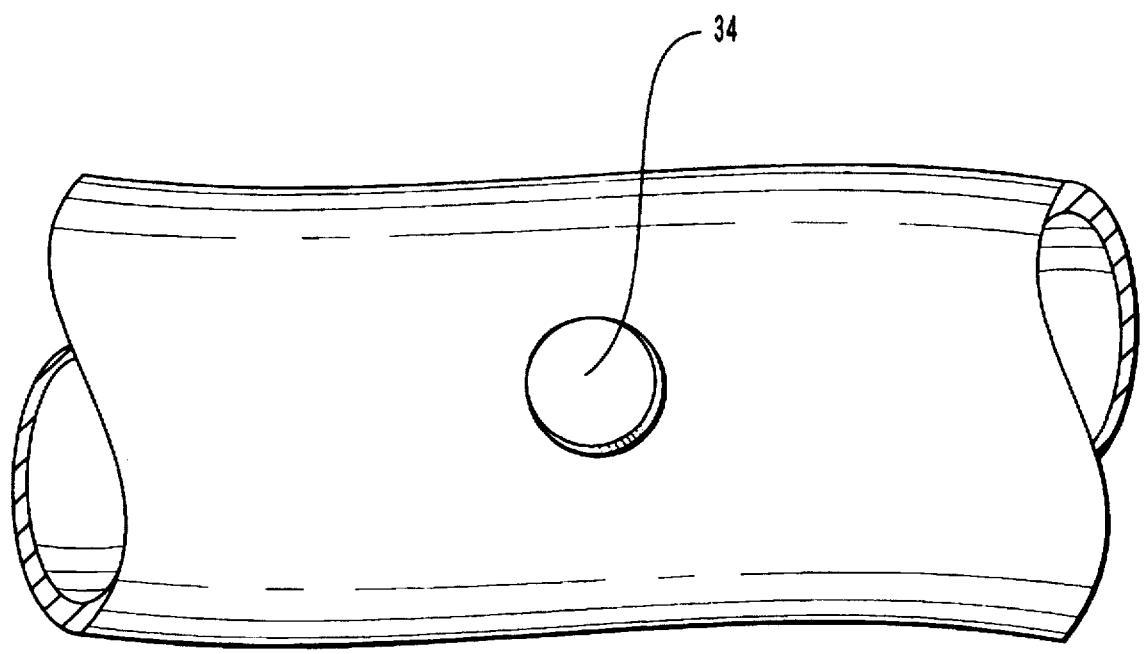
FIG. 7 is an illustration of an aortotomy resulting from an aortic punch used in concert with an incision such as provided in FIG. 6.

FIG. 6, for example, illustrates a stabbed cruciate incision 30 through an aorta 32 made by the aortic knife of FIG. 3. FIG. 7 illustrates the resulting aortotomy 34 after the utilization of an aortic punch preferably sized to correspond to the size of the aortic knife. The aortotomy 34 is substantially uniform and circular in shape and clearly lacks the lateral nicks of the prior art.

Figure 8:
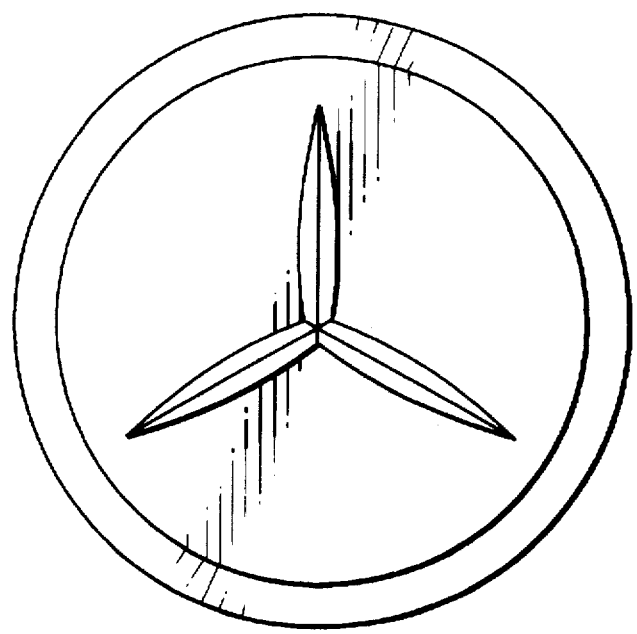
FIG. 8 is an end view of an alternate embodiment of the blade configuration of an aortic knife in accordance with the present invention.
Figure 9:
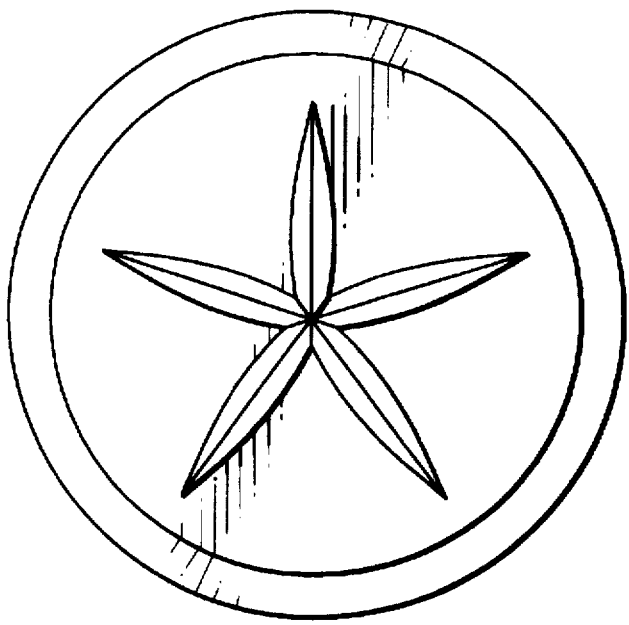
FIG. 9 is an end view of yet another alternate embodiment of the blade configuration of an aortic knife in accordance with the present invention.

Alternatively, an aortic knife in accordance with the present invention may comprise any number of blades, and preferably comprises at least three. It is further preferred that the arrangement of the blades around the sharpened distal point of the blade portion of the knife is such that the angles separating the blades are equal. For example, in an embodiment comprising three surgical blades, each blade is separated from each other blade by about 120 degrees. FIG. 8 illustrates an end view of such a three-bladed configuration. In an alternate embodiment illustrated in FIG. 9, the surgical blades are configured into a stellate, or star-shape, configuration with five blades radiating outwardly at about 72 degree angles.

It should be appreciated that the blades can alternatively be separated from each other by angles of differing degrees. Equal angles are preferred, but the present invention is not limited to such a configuration.

Various sizes of the aortic knife are available. It is preferred that aortic knives in accordance with the present invention are sized with respect to the various diameters of aortic punches available. Essentially, the aortic knife will be sized such that each knife diameter corresponds to an aortic punch size so that a surgeon can customize a desired fit. This offers uniform and precise incisions, and eliminates the lateral nicks associated with the conventional technique.

It is preferred that the knife be slightly smaller in diameter than the corresponding punch with which it is to be used. Once the anvil of the punch is inside the aorta, the shaft of the punch is centered and the punch is fired. It has been found that aortotomy punch sites created in this manner are much more uniform than those created with the conventional methods.

The present invention also relates to a method for using the aortic knife to facilitate creation of an aortotomy. A graft of a suitable diameter for use with a by-pass graft is dissected, brought to the aorta, and cut to an appropriate length. Antegrade cardioplegia is preferably supplied such that the aorta is filled and pressurized; the aorta is preferably full at the time of use of the aortic knife. A proximal anastomotic site is selected and the surrounding tissue is removed. An aortic punch is selected according to the diameter desired for the anastomosis. An aortic knife is then selected to advantageously correspond to the diameter of the aortic punch. A four-sided aortic knife is preferably passed perpendicularly into the aorta creating a cruciate, or "+" shaped, incision in the aorta. An anvil of an aortic punch is then placed through the cruciate incision. The punch is centered and fired. Care is taken to avoid the back or opposite wall of the aorta.

An aortic knife in accordance with the present invention may alternatively be used to facilitate placement of an aortic cannula. In the preferred embodiment of the present invention, the incision opens in four directions as opposed to the linear incision associated with conventional scalpel techniques. Cannulation sites using the aortic knife and method associated therewith experience fewer problems with de-cannulation than those using conventional techniques. In addition, the method and apparatus of the present invention frequently provide a decrease in bleeding around the cannula at a cannulation site.

The present invention may be embodied in other specific forms without departing from its spirit or essential characteristics. The described embodiments are to be considered all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for effectuating improved aortic incisions comprising the steps of:
   a. determining a site on an aorta for an aortotomy, wherein the resulting arteriotomy will be of a size suitable for an anastomosis to be performed thereon;
   b. obtaining an aortic punch suitable in size for the aortotomy site, said aortic punch further comprising an anvil for insertion through an incision in an aorta;
   c. obtaining an aortic knife suitable for use with the selected aortic punch, said aortic knife having a plurality of surgical blades radiating outwardly and proximally from a distal sharpened point, and having a smaller diameter than the diameter of the anvil of said aortic punch; and
   d. inserting the aortic knife perpendicularly into the predetermined site on the aorta, thus effectuating a multi-sided incision.

2. A method as recited in claim 1, wherein the aorta is substantially full of fluid during insertion of the aortic knife therein.

3. A method as recited in claim 1, wherein the anvil of the aortic punch is inserted through the multi-sided incision created by the aortic knife.

4. A method as recited in claim 3, wherein the aortic punch is centered in the multi-sided incision created by the aortic knife.

5. A method as recited in claim 4, wherein the aortic punch is fired to create a substantially uniform aortotomy.

6. A method for effectuating improved aortic incisions for cannulation, comprising the steps of:
   a. obtaining a surgical knife, said knife having a plurality of surgical blades radiating outwardly and proximally from a distal sharpened point;
   b. inserting said knife into a vessel to create a multi-sided incision; and
   c. inserting a cannula through the multi-sided incision in the vessel.

7. A method as recited in claim 6, wherein cannulation through the multi-sided incision diminishes blood loss therefrom.

\* \* \* \* \*

UNITED STATES PATENT AND TRADEMARK OFFICE
CERTIFICATE OF CORRECTION

PATENT NO. : 5,893,865

DATED : Apr. 13, 1999

INVENTOR(S) : Carl A. Swindle; John C. Alexander, Jr.

It is certified that error appears in the above-identified patent and that said Letters Patent is hereby corrected as shown below:

Cover Page, left column, insert the following under U.S. Patent Documents:

| | | |
|---|---|---|
| 4,365,957 | 12/1982 | Das |
| 5,797,944 | 8/1998 | Nobels et al. |
| 5,554,167 | 9/1996 | Young |
| 4,873,976 | 10/1989 | Schreiber |
| 4,018,228 | 4/1977 | Goosen |
| 4,468,038 | 8/1984 | Saunders |
| 4,570,941 | 2/1986 | Saunders |
| Des. 291,595 | 8/1997 | Armstrong |
| 2,649,860 | 8/1953 | Royer |
| Des. 332,492 | 1/1993 | Rosenberg et al. |
| 4,349,202 | 9/1982 | Scott |
| 5,135,525 | 8/1992 | Biscoping et al. |
| 5,196,024 | 3/1993 | Barath |
| 5,275,583 | 1/1994 | Crainich |
| 5,447,516 | 9/1995 | Gardner |
| 5,735,290 | 4/1998 | Sterman et al. |
| 4,832,045 | 5/1989 | Goldberger |
| 4,891,887 | 1/1990 | Witte |
| 4,862,591 | 9/1989 | Barringer |
| 5,066,288 | 11/1991 | Deniegar et al. |
| 5,452,733 | 9/1995 | Sterman et al. |
| 5,507,765 | 4/1996 | Mott |
| 5,554,137 | 9/1996 | Young et al. |
| 5,591,186 | 1/1997 | Wurster et al. |

UNITED STATES PATENT AND TRADEMARK OFFICE
CERTIFICATE OF CORRECTION

PATENT NO. : 5,893,865
DATED : Apr. 13, 1999
INVENTOR(S) : Carl A. Swindle; John C. Alexander, Jr.

It is certified that error appears in the above-identified patent and that said Letters Patent is hereby corrected as shown below:

| 5,591,192 | 1/1997 | Privitera et al. |
| 5,609,604 | 3/1997 | Schwemberger et al. |

Col. 5, line 14, after "considered" insert --in--

Signed and Sealed this

Twenty-first Day of December, 1999

Attest:

Attesting Officer

Q. TODD DICKINSON

Acting Commissioner of Patents and Trademarks